US012780879B2

(12) United States Patent
Sun et al.

(10) Patent No.: US 12,780,879 B2
(45) Date of Patent: Nov. 3, 2026

(54) ATTENUATION METHOD OF INFLUENZA VIRUS, ATTENUATED INFLUENZA VIRUS STRAIN, AND USE THEREOF

(71) Applicant: DIFFERENCE BIOTECH PTE.LTD., Singapore (SG)

(72) Inventors: Huimin Sun, Hangzhou (CN); Fei Yu, Hangzhou (CN); Mengyun Zhou, Hangzhou (CN); Shuihua Mao, Hangzhou (CN); Chenjie Fang, Hangzhou (CN); Jiasheng Song, Hangzhou (CN)

(73) Assignee: DIFFERENCE BIOTECH PTE. LTD., Singapore (SG)

( * ) Notice: Subject to any disclaimer, the term of this patent is extended or adjusted under 35 U.S.C. 154(b) by 733 days.

(21) Appl. No.: 18/029,677

(22) PCT Filed: Apr. 29, 2022

(86) PCT No.: PCT/CN2022/090199

§ 371 (c)(1),
(2) Date: Mar. 31, 2023

(87) PCT Pub. No.: WO2023/142285

PCT Pub. Date: Aug. 3, 2023

(65) Prior Publication Data

US 2024/0360180 A1 Oct. 31, 2024

(30) Foreign Application Priority Data

Jan. 27, 2022 (CN) ......................... 202210100598.6

(51) Int. Cl.

| | |
|---|---|
| ***C07K 14/005*** | (2006.01) |
| ***A61K 39/00*** | (2006.01) |
| ***A61K 39/145*** | (2006.01) |
| ***A61P 31/16*** | (2006.01) |
| ***C12N 7/00*** | (2006.01) |
| ***C12N 15/85*** | (2006.01) |

(52) U.S. Cl.

CPC .......... *C07K 14/005* (2013.01); *A61K 39/145* (2013.01); *A61P 31/16* (2018.01); *C12N 7/00* (2013.01); *C12N 15/85* (2013.01); *A61K 2039/5254* (2013.01); *C12N 2760/16122* (2013.01); *C12N 2760/16134* (2013.01); *C12N 2760/16162* (2013.01); *C12N 2800/107* (2013.01)

(58) Field of Classification Search

CPC .......... A61K 39/145; A61K 2039/5254; C12N 2760/16134; C07K 14/005

See application file for complete search history.

(56) References Cited

U.S. PATENT DOCUMENTS

| | | | | |
|---|---|---|---|---|
| 2009/0074812 A1* | 3/2009 | Watanabe | C07K 14/005 | 435/235.1 |
| 2011/0236417 A1* | 9/2011 | Watanabe | A61P 31/16 | 424/199.1 |
| 2019/0365882 A1* | 12/2019 | Seong | C12N 15/52 | |

FOREIGN PATENT DOCUMENTS

| | | |
|---|---|---|
| CN | 109652430 A | 4/2019 |
| CN | 114381438 A | 4/2022 |
| WO | 0003019 A1 | 1/2000 |

OTHER PUBLICATIONS

Sarawar, S., Hatta, Y., Watanabe, S., Dias, P., Neumann, G., Kawaoka, Y., and Bilsel, P., M2SR, a novel live single replication influenza virus vaccine, provides effective heterosubtypic protection in mice, Sep. 30, 2016, Vaccine, 34(42): 5090-5098 (Year: 2016).*

Shinji Watanabe, et al., Influenza A Virus Lacking M2 Protein as a Live Attenuated Vaccine, Journal of Virology, 2009, pp. 5947-5950, vol. 83, No. 11.

Nicholas Wohlgemuth, et al., The M2 protein of live, attenuated influenza vaccine encodes a mutation that reduces replication in human nasal epithelial cells, Vaccine, 2017, pp. 1-18, vol. 35, No. 48.

Hou Tian-Long, et al., Interaction between M1 and M2 Proteins of Influenza Virus and its Role in Virus Budding, Chinese Journal of Animal Infectious Disease, 2016, pp. 1-5, vol. 24 No. 6.

* cited by examiner

*Primary Examiner* — Michael Allen
*Assistant Examiner* — Kristina E. Ly
(74) *Attorney, Agent, or Firm* — Bayramoglu Law Offices LLC

(57) ABSTRACT

An attenuation method of an influenza virus, an attenuated influenza virus strain, and the use thereof are provided. The attenuation method includes the following step: deleting a random number of bases at a random position for a transmembrane domain and a cytoplasmic domain of an M2 protein in a conserved region of the influenza virus to obtain an attenuated influenza virus with a corresponding base deletion. An attenuated influenza virus strain prepared by the attenuation method exhibits prominent growth characteristics on an M2 protein-expressing MDCK cell line; and the virus strain at a high dose can grow in an MDCK cell or a chicken embryo and has a high agglutination titer of chicken red blood cells (CRBCs). Results of nasal challenge of Balb/C mice show that the virus strain is non-pathogenic to mice compared with the parental virus IAV PR8.

4 Claims, 3 Drawing Sheets
(3 of 3 Drawing Sheet(s) Filed in Color)
Specification includes a Sequence Listing.

SEQUENCE LISTING

<160> NUMBER OF SEQ ID NOS: 21

<210> SEQ ID NO 1
<211> LENGTH: 280
<212> TYPE: DNA
<213> ORGANISM: Artificial Sequence
<220> FEATURE:
<223> OTHER INFORMATION: The sequence is synthetized.

<400> SEQUENCE: 1
atgagtcttc taaccgaggt cgaaacgcct atcagaaacg aatgggggtg cagatgcaac 60
ggttcaagtg atcgcaaata tcattgggat cttgcacttg acattgtgga ttcttgatcg 120 tcttttttc aaatgcattt accgtcgctt taaatacgga ctgaaaggag ggccttctac 180
ggaaggagtg ccaaagtcta tgagggaaga atatcgaaag gaacagcaga gtgctgtgga 240
tgctgacgat ggtcattttg tcagcataga gctggagtaa 280

<210> SEQ ID NO 2
<211> LENGTH: 274
<212> TYPE: DNA
<213> ORGANISM: Artificial Sequence
<220> FEATURE:
<223> OTHER INFORMATION: The sequence is synthetized.

<400> SEQUENCE: 2
atgagtcttc taaccgaggt cgaaacgcct atcagaaacg aatgggggtg cagatgcaac 60
ggttcaagtg atcctctcac tattgctgca cttgacattg tggattcttg atcgtctttt 120
tttcaaatgc atttaccgtc gctttaaata cggactgaaa ggagggcctt ctacggaagg 180
agtgccaaag tctatgaggg aagaatatcg aaaggaacag cagagtgctg tggatgctga 240
cgatggtcat tttgtcagca tagagctgga gtaa 274

<210> SEQ ID NO 3
<211> LENGTH: 272
<212> TYPE: DNA
<213> ORGANISM: Artificial Sequence
<220> FEATURE:
<223> OTHER INFORMATION: The sequence is synthetized.

<400> SEQUENCE: 3
atgagtcttc taaccgaggt cgaaacgcct atcagaaacg aatgggggtg cagatgcaac 60
ggttcaagtg atcctctcac tattgccgca aatatcattg ggatcttgca cttgacattg 120
tggattcttt ttaccgtcgc tttaaatacg gactgaaagg agggccttct acggaaggag 180
tgccaaagtc tatgagggaa gaatatcgaa aggaacagca gagtgctgtg gatgctgacg 240
atggtcattt tgtcagcata gagctggagt aa 272

<210> SEQ ID NO 4
<211> LENGTH: 256
<212> TYPE: DNA
<213> ORGANISM: Artificial Sequence
<220> FEATURE:
<223> OTHER INFORMATION: The sequence is synthetized.

<400> SEQUENCE: 4
atgagtcttc taaccgaggt cgaaacgcct atcagaaacg aatgggggtg cagatgcaac 60
ggttcaagtg atcctctcac tattgccgca aatatcattg ggatcttgca cttgacattg 120
tggattcttg atcgtctttt tttcaaatgc atctacggaa ggagtgccaa agtctatgag 180
ggaagaatat cgaaaggaac agcagagtgc tgtggatgct gacgatggtc attttgtcag 240
catagagctg gagtaa 256

<210> SEQ ID NO 5
<211> LENGTH: 229
<212> TYPE: DNA
<213> ORGANISM: Artificial Sequence
<220> FEATURE:
<223> OTHER INFORMATION: The sequence is synthetized.

<400> SEQUENCE: 5
atgagtcttc taaccgaggt cgaaacgcct atcagaaacg aatgggggtg cagatgcaac 60
ggttcaagtg atcctctcac tattgcttta ccgtcgcttt aaatacggac tgaaaggagg 120
gccttctacg gaaggagtgc caaagtctat gagggaagaa tatcgaaagg aacagcagag 180
tgctgtggat gctgacgatg gtcattttgt cagcatagag ctggagtaa 229

<210> SEQ ID NO 6
<211> LENGTH: 191
<212> TYPE: DNA
<213> ORGANISM: Artificial Sequence
<220> FEATURE:
<223> OTHER INFORMATION: The sequence is synthetized.

<400> SEQUENCE: 6
atgagtcttc taaccgaggt cgaaacgcct atcagaaacg aatgggggtg cagatgcaac 60
ggttcaagtg atcctctcac tattgctcta cggaaggagt gccaaagtct atgagggaag 120
aatatcgaaa ggaacagcag agtgctgtgg atgctgacga tggtcatttt gtcagcatag 180
agctggagta a 191

<210> SEQ ID NO 7
<211> LENGTH: 294
<212> TYPE: DNA
<213> ORGANISM: Artificial Sequence
<220> FEATURE:
<223> OTHER INFORMATION: The sequence is synthetized.

<400> SEQUENCE: 7
atgagtcttc taaccgaggt cgaaacgcct atcagaaacg aatgggggtg cagatgcaac 60
ggttcaagtg atcctctcac tattgccgca aatatcattg ggatcttgca cttgacattg 120
tggattcttg atcgtctttt tttcaaatgc atttaccgtc gctttaaata cggactgaaa 180
ggagggcctt ctacggaagg agtgccaaag tctatgaggg aagaatatcg aaaggaacag 240
cagagtgctg tggatgctga cgatggtcat tttgtcagca tagagctgga gtaa 294

<210> SEQ ID NO 8
<211> LENGTH: 37
<212> TYPE: DNA
<213> ORGANISM: Artificial Sequence
<220> FEATURE:
<223> OTHER INFORMATION: The sequence is synthetized.

<400> SEQUENCE: 8
aacggttcaa gtgatcgcaa atatcattgg gatcttg 37

<210> SEQ ID NO 9
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 9
atcacttgaa ccgttgcatc tg 22

<210> SEQ ID NO 10
<211> LENGTH: 39
<212> TYPE: DNA
<213> ORGANISM: Artificial Sequence
<220> FEATURE:
<223> OTHER INFORMATION: The sequence is synthetized.

<400> SEQUENCE: 10
tcctctcact attgctgcac ttgacattgt ggattcttg 39

<210> SEQ ID NO 11
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 11
gcaatagtga gaggatcact tg 22

<210> SEQ ID NO 12
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 12
acattgtgga ttctttttac cgtcgcttta aatacg 36

<210> SEQ ID NO 13
<211> LENGTH: 21
<212> TYPE: DNA
<213> ORGANISM: Artificial Sequence
<220> FEATURE:
<223> OTHER INFORMATION: The sequence is synthetized.

<400> SEQUENCE: 13
aagaatccac aatgtcaagt g 21

<210> SEQ ID NO 14
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 14
tttttttcaa atgcatctac ggaaggagtg ccaaag 36

<210> SEQ ID NO 15
<211> LENGTH: 19
<212> TYPE: DNA
<213> ORGANISM: Artificial Sequence
<220> FEATURE:

<223> OTHER INFORMATION: The sequence is synthetized.

<400> SEQUENCE: 15
tgcatttgaa aaaaagacg 19

<210> SEQ ID NO 16
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 16
tcctctcact attgctttac cgtcgcttta aatacg 36

<210> SEQ ID NO 17
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 17
gcaatagtga gaggatcact tg 22

<210> SEQ ID NO 18
<211> LENGTH: 36
<212> TYPE: DNA
<213> ORGANISM: Artificial Sequence
<220> FEATURE:
<223> OTHER INFORMATION: The sequence is synthetized.

<400> SEQUENCE: 18
tcctctcact attgctctac ggaaggagtg ccaaag 36

<210> SEQ ID NO 19
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 19
gcaatagtga gaggatcact tg 22

<210> SEQ ID NO 20
<211> LENGTH: 31
<212> TYPE: DNA
<213> ORGANISM: Artificial Sequence
<220> FEATURE:
<223> OTHER INFORMATION: The sequence is synthetized.

<400> SEQUENCE: 20
cacacacgtc tccgggagca aaagcaggta g 31

<210> SEQ ID NO 21
<211> LENGTH: 38
<212> TYPE: DNA
<213> ORGANISM: Artificial Sequence
<220> FEATURE:
<223> OTHER INFORMATION: The sequence is synthetized.

<400> SEQUENCE: 21
cacacacgtc tcctattagt agaaacaagg tagtttt 38

ATTENUATION METHOD OF INFLUENZA VIRUS, ATTENUATED INFLUENZA VIRUS STRAIN, AND USE THEREOF

CROSS REFERENCE TO THE RELATED APPLICATIONS

This application is the national phase entry of International Application No. PCT/CN2022/090199, filed on Apr. 29, 2022, which is based upon and claims priority to Chinese Patent Application No. 202210100598.6, filed on Jan. 27, 2022, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBHZZJ012-PKG_Sequence_Listing.txt, created on Mar. 6, 2023, and is 6,593 bytes in size.

TECHNICAL FIELD

The present disclosure relates to the technical field of biomedicine and specifically relates to an attenuation method of an influenza virus, an attenuated influenza virus strain, and the use thereof.

BACKGROUND

Influenza A (IA) is a highly contagious acute respiratory disease caused by an influenza A virus (IAV), which is a segmented negative-stranded RNA virus of the orthomyxoviridae family. Vaccination is the main means for preventing IAV infection, and inactivated and live-attenuated vaccines are currently available. Due to limited mucosal immune responses and cytotoxic T-cell responses, a protective effect of an inactivated vaccine lasts only for a short period of time, and thus the inactivated vaccine needs to be given once a year. In contrast, an IAV live-attenuated vaccine can cause strong mucosal and cellular immune responses through nasal immunization, and thus a protective effect of the IAV live-attenuated vaccine can last for a long period of time. There are only two live-attenuated vaccines currently on the market that are based on a cold-adapted virus strain, and these two vaccines can only be used for people between the ages of 2 and 49. Therefore, it is necessary to develop a safe and effective live-attenuated vaccine to fight against IAV infection.

SUMMARY

An objective of the present disclosure is to provide an attenuation method of an influenza virus, an attenuated influenza virus strain, and the use thereof. An attenuated influenza virus strain (a replication-restricted virus) prepared by the attenuation method of the present disclosure can exhibit prominent growth characteristics on an M2 protein-expressing MDCK cell line, and is non-pathogenic to mice compared with a parental virus, which can lay a foundation for the screening of safe and effective IAV live-attenuated vaccines. The attenuated influenza virus strain can also grow well on an MDCK cell or a chicken embryo, and the replication-restricted virus at a high dose can grow well on the MDCK cell or the chicken embryo, which makes it possible to produce an attenuated virus with a chicken embryo in large quantities.

The present disclosure provides an attenuation method of an influenza virus, including the following step: deleting a random number of bases at a random position for a transmembrane domain and a cytoplasmic domain of an M2 protein in a conserved region of the influenza virus to obtain an attenuated influenza virus with a corresponding base deletion.

Preferably, a parental virus targeted by the attenuation method includes A/Puerto Rico/8/1934.

Preferably, the deleting a random number of bases at a random position refers to one selected from the group consisting of (a) to (f):

(a) deleting 14 bases from position 73 to position 86 of a coding region for the M2 protein;
(b) deleting 20 bases from position 87 to position 106 of a coding region for the M2 protein;
(c) deleting 22 bases from position 130 to position 151 of a coding region for the M2 protein;
(d) deleting 38 bases from position 152 to position 189 of a coding region for the M2 protein;
(e) deleting 65 bases from position 87 to position 151 of a coding region for the M2 protein; and
(f) deleting 103 bases from position 87 to position 189 of a coding region for the M2 protein.

The present disclosure also provides an attenuated influenza virus strain prepared by the attenuation method described in the technical solution, and the attenuated influenza virus strain is prepared as follows: with A/Puerto Rico/8/1934 as a parental virus, subjecting the M2 protein to one base deletion selected from the group consisting of (a) to (f):

(a) deleting 14 bases from position 73 to position 86 of a coding region for the M2 protein;
(b) deleting 20 bases from position 87 to position 106 of a coding region for the M2 protein;
(c) deleting 22 bases from position 130 to position 151 of a coding region for the M2 protein;
(d) deleting 38 bases from position 152 to position 189 of a coding region for the M2 protein;
(e) deleting 65 bases from position 87 to position 151 of a coding region for the M2 protein; and
(f) deleting 103 bases from position 87 to position 189 of a coding region for the M2 protein.

Preferably, a coding region for an M2 protein of the attenuated influenza virus strain has a nucleotide sequence shown in SEQ ID NO: 1, SEQ ID NO: 2, SEQ ID NO: 3, SEQ ID NO: 4, SEQ ID NO: 5, or SEQ ID NO: 6.

The present disclosure also provides a group of plasmids for constructing an attenuated influenza virus strain, and the plasmids include nucleotide sequences shown in SEQ ID NO: 1, SEQ ID NO: 2, SEQ ID NO: 3, SEQ ID NO: 4, SEQ ID NO: 5, and SEQ ID NO: 6, respectively.

Preferably, a basal plasmid for constructing the plasmids includes a nucleotide sequence shown in SEQ ID NO: 7.

The present disclosure also provides primers for constructing the plasmids described in the technical solution, and the primers have nucleotide sequences shown in SEQ ID NOS: 8-19.

The present disclosure also provides a use of the attenuation method described in the technical solution, the attenuated influenza virus strain described in the technical solution, the plasmids described in the technical solution, or the primers described in the technical solution in preparation of a live-attenuated influenza vaccine.

The present disclosure provides an attenuation method of an influenza virus. An attenuated influenza virus strain (a replication-restricted virus) prepared by the attenuation method of the present disclosure can exhibit prominent growth characteristics on an M2 protein-expressing MDCK cell line, and is non-pathogenic to mice compared with a parental virus, which can lay a foundation for the screening of safe and effective IAV live-attenuated vaccines. The attenuated influenza virus strain can also grow well on an MDCK cell or a chicken embryo, and the replication-restricted virus at a high dose can grow well on the MDCK cell or the chicken embryo, which makes it possible to produce an attenuated virus with a chicken embryo in large quantities.

BRIEF DESCRIPTION OF THE DRAWINGS

The application file contains at least one drawing executed in color. Copies of this patent or patent application publication with color drawing(s) will be provided by the Office upon request and payment of the necessary fee.

DETAILED DESCRIPTION OF THE EMBODIMENTS

Figure 1:
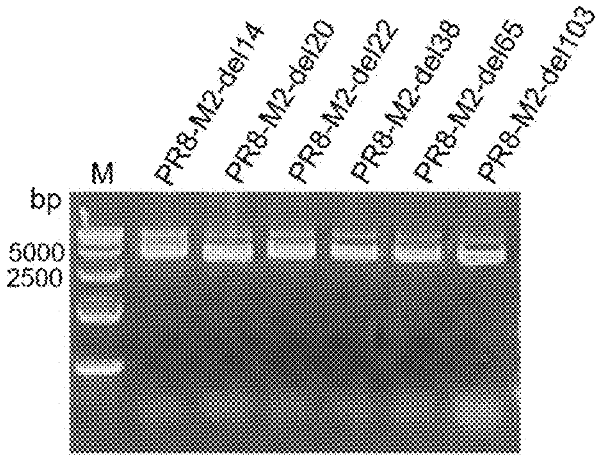
FIG. 1 shows agarose gel electrophoresis results of the extracted plasmids PR8-M2-del14, PR8-M2-de120, PR8-M2-del22, PR8-M2-del38, PR8-M2-del65, and PR8-M2-del103 according to the present disclosure.

The present disclosure provides an attenuation method of an influenza virus, including the following step: deleting a random number of bases at a random position for a transmembrane domain and a cytoplasmic domain of an M2 protein in a conserved region of the influenza virus to obtain an attenuated influenza virus with a corresponding base deletion.

In the present disclosure, a reverse genetic system is preferentially used to generate a series of random base deletions for a transmembrane domain (TM) and a cytoplasmic domain (CT), and the toxicity of a virus with a random deletion is evaluated, which can facilitate the acquisition of a safe and effective IAV live-attenuated vaccine.

In the present disclosure, a parental virus targeted by the attenuation method preferably includes A/Puerto Rico/8/1934 (abbreviated IAV PR8).

In the present disclosure, the deleting a random number of bases at a random position preferably refers to one selected from the group consisting of (a) to (f):

(a) deleting 14 bases from position 73 to position 86 of a coding region for the M2 protein, where the coding region has a nucleotide sequence shown in SEQ ID NO: 1;

(b) deleting 20 bases from position 87 to position 106 of a coding region for the M2 protein, where the coding region has a nucleotide sequence shown in SEQ ID NO: 2;

(c) deleting 22 bases from position 130 to position 151 of a coding region for the M2 protein, where the coding region has a nucleotide sequence shown in SEQ ID NO: 3;

(d) deleting 38 bases from position 152 to position 189 of a coding region for the M2 protein, where the coding region has a nucleotide sequence shown in SEQ ID NO: 4;

(e) deleting 65 bases from position 87 to position 151 of a coding region for the M2 protein, where the coding region has a nucleotide sequence shown in SEQ ID NO: 5; and (f) deleting 103 bases from position 87 to position 189 of a coding region for the M2 protein, where the coding region has a nucleotide sequence shown in SEQ ID NO: 6.

An attenuated influenza virus strain prepared by the attenuation method of the present disclosure can grow well on an MDCK cell or a chicken embryo. Balb/C mice are nasal challenged with the attenuated influenza virus strain, and then the body weight changes and survival are observed and the viral loads in turbinates and lungs are detected. Results show that the attenuated influenza virus strain is non-pathogenic to mice compared with the parental virus IAV PR8. The attenuation method of the present disclosure lays a foundation for the screening of safe and effective IAV live-attenuated vaccines.

The present disclosure also provides an attenuated influenza virus strain prepared by the attenuation method described in the technical solution, and the attenuated influenza virus strain is prepared as follows: with A/Puerto Rico/8/1934 as a parental virus, subjecting the M2 protein to one base deletion selected from the group consisting of (a) to (f):

(a) deleting 14 bases from position 73 to position 86 of a coding region for the M2 protein;

(b) deleting 20 bases from position 87 to position 106 of a coding region for the M2 protein;

(c) deleting 22 bases from position 130 to position 151 of a coding region for the M2 protein;

(d) deleting 38 bases from position 152 to position 189 of a coding region for the M2 protein;

(e) deleting 65 bases from position 87 to position 151 of a coding region for the M2 protein; and (f) deleting 103 bases from position 87 to position 189 of a coding region for the M2 protein.

In the present disclosure, a coding region for an M2 protein of the attenuated influenza virus strain has a nucleotide sequence shown in SEQ ID NO: 1, SEQ ID NO: 2, SEQ ID NO: 3, SEQ ID NO: 4, SEQ ID NO: 5, or SEQ ID NO: 6.

The present disclosure also provides a group of plasmids for constructing an attenuated influenza virus strain, and the plasmids include nucleotide sequences shown in SEQ ID NO: 1, SEQ ID NO: 2, SEQ ID NO: 3, SEQ ID NO: 4, SEQ ID NO: 5, and SEQ ID NO: 6, respectively. The plasmids of the present disclosure are random base deletion plasmids for the M2 gene. The present disclosure has no special limitations on a construction method of the deletion plasmids, and a conventional construction method of the deletion plasmids well known to those skilled in the art may be adopted. In the present disclosure, a basal plasmid for constructing the plasmids preferably includes a nucleotide sequence shown in SEQ ID NO: 7. The present disclosure has no special limitations on a type of the basal plasmid, as long as the basal plasmid includes a nucleotide sequence shown in SEQ ID NO: 7.

The present disclosure also provides primers for constructing the plasmids described in the technical solution, and the primers have nucleotide sequences shown in SEQ ID NOS: 8-19.

The present disclosure also provides a use of the attenuation method described in the technical solution, the attenuated influenza virus strain described in the technical solution, the plasmids described in the technical solution, or the primers described in the technical solution in preparation of a live-attenuated influenza vaccine.

The attenuation method of an influenza virus, the attenuated influenza virus strain, and the use thereof according to the present disclosure will be further described in detail below with reference to specific examples. The technical solutions of the present disclosure include, but are not limited to, the following examples.

Example 1

Construction of Random Base Deletion Plasmids for an M2 Gene of an Influenza Virus Plasmids expressing the M2 gene of the influenza virus strain PR8 were extracted (the present disclosure has no special limitations on the construction method of the plasmid, and an M2-expressing plasmid can be constructed by a conventional recombinant plasmid construction method with a common plasmid well known by those skilled in the art and the M gene), and PCR amplification was conducted with a series of base deletion primers (primer sequences were shown in Table 1). After a molecular weight was identified by agarose gel electrophoresis to be correct, a target gel band was recovered and subjected to recombination at 50° C. for 15 min, a recombination product was transformed into an *Escherichia coli* (*E. coli*) competent cell, and colonies were picked for sequencing; and after a correct sequence was determined, the following deletion plasmids were successfully prepared with endotoxin-free small and medium kits: PR8-M2-del14, PR8-M2-del20, PR8-M2-del22, PR8-M2-del38, PR8-M2-del65, and PR8-M2-del103 (agarose gel electrophoresis results of the extracted plasmids PR8-M2-del14, PR8-M2-del20, PR8-M2-del22, PR8-M2-del38, PR8-M2-del65, and PR8-M2-del103 were shown in FIG. 1).

TABLE 1

Specific primer sequences

| Deletion plasmid name | Primer name | Primer sequence (5'-3') |
|---|---|---|
| PR8-M2-del14 | Del14-F | aacggttcaagtgatcgcaaatatcattgggatcttg (SEQ ID NO: 8) |
| | Del14-R | atcacttgaaccgttgcatctg (SEQ ID NO: 9) |
| PR8-M2-del20 | Del20-F | tcctctcactattgctgcacttgacattgtggat-tcttg (SEQ ID NO: 10) |
| | Del20-R | gcaatagtgagaggatcacttg (SEQ ID NO: 11) |
| PR8-M2-del22 | Del22-F | acattgtggattctttttaccgtcgctttaaatacg (SEQ ID NO: 12) |
| | Del22-R | aagaatccacaatgtcaagtg (SEQ ID NO: 13) |
| PR8-M2-del38 | Del38-F | tttttttcaaatgcatctacggaaggagtgccaaag (SEQ ID NO: 14) |
| | Del38-R | tgcatttgaaaaaaagacg (SEQ ID NO: 15) |
| PR8-M2-del65 | Del65-F | tcctctcactattgctttaccgtcgctttaaatacg (SEQ ID NO: 16) |
| | Del65-R | gcaatagtgagaggatcacttg (SEQ ID NO: 17) |
| PR8-M2-del103 | Del103-F | tcctctcactattgctctacggaaggagtgccaaag (SEQ ID NO: 18) |
| | Del103-R | gcaatagtgagaggatcacttg (SEQ ID NO: 19) |

Example 2

Rescue and Verification of Replication-Restricted Influenza Viruses

An HEK293T cell was inoculated into a special six-well plate of Thermo Fisher, and 12 h later, the plasmids including 7 genes of PR8 (pFlu-PR8-PB2, pFlu-PR8-PB1, pFlu-PR8-PA, pFlu-PR8-NP, pFlu-PR8-NS, pFlu-PR8-HA, and pFlu-PR8-NA), each of the series of random base deletion plasmids for the M2 gene constructed in Example 1, and the M2 protein-expressing plasmid were co-transfected into the HEK293T cell; 6 h to 8 h after the transfection, a medium was changed; 48 h after the transfection, the cell plate was frozen and thawed once, and a culture supernatant was collected and inoculated in a T25 culture flask with the M2 protein-expressing MDCK cell; and 72 h to 96 h after the inoculation, the CPE was observed, the culture flask was frozen and thawed once and then centrifuged, and a resulting supernatant was collected. Resulting replication-restricted influenza viruses were named rPR8-M2-del14, rPR8-M2-del20, rPR8-M2-del22, rPR8-M2-del38, rPR8-M2-del65, and rPR8-M2-del103, respectively.

Figure 2:
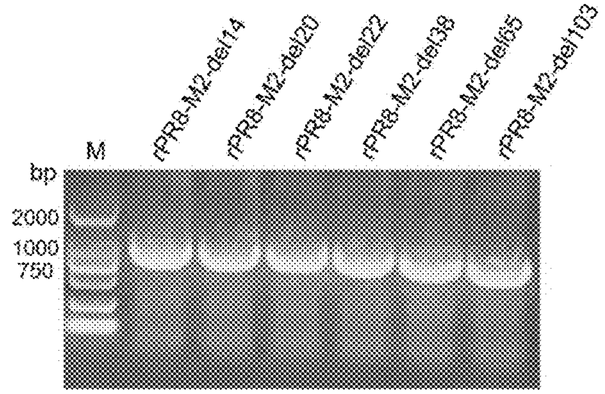
FIG. 2 shows agarose gel electrophoresis results of the replication-restricted viruses rPR8-M2-del14, rPR8-M2-del20, rPR8-M2-del22, rPR8-M2-del38, rPR8-M2-del65, and rPR8-M2-del103 identified by RT-PCR according to the present disclosure.

A viral RNA obtained above was extracted using a viral RNA extraction kit, and RT-PCR amplification was conducted with the primers in Table 2; and after a molecular weight was identified by agarose gel electrophoresis to be correct (FIG. 2), a PCR product was sequenced, and sequencing results showed that the virus was a replication-restricted virus with a corresponding base deletion. FIG. 2 shows agarose gel electrophoresis results of the replication-restricted viruses rPR8-M2-del14, rPR8-M2-del20, rPR8-M2-del22, rPR8-M2-del38, rPR8-M2-del65, and rPR8-M2-del103 identified by RT-PCR.

TABLE 2

Identified primer sequences

| Primer name | Primer sequence (5'-3') |
|---|---|
| Bm-M-F1 | cacacacgtctccgggagcaaaagcaggtag (SEQ ID NO: 20) |
| Bm-M-R1027 | cacacacgtctcctattagtagaaacaaggtagtttt (SEQ ID NO: 21) |

Example 3

Determination of Titers of Replication-Restricted Influenza Viruses

The M2 protein-expressing MDCK cell was inoculated into a 96-well plate; after the cell grew to form a monolayer, 50 μL of a replication-restricted influenza virus was added to 450 μL of 1% TPCK opi-MEM, and a resulting mixture was thoroughly shaken to obtain a system 1 with a final concentration of 10-1; 50 μL of the system 1 was taken and added to 450 μL of 1% TPCK opi-MEM, and a resulting mixture was thoroughly shaken to obtain a system 2 with a final concentration of 10-2; in this way, the virus solution was continuously diluted 10-fold to 10-19, then a medium in the 96-well plate was removed, the plate was washed with PBS, and 100 μL of a virus solution with a corresponding dilution ratio was added to each well, where 3 replicates were set for each dilution ratio; the cell was cultivated for 72 h in a cell culture incubator at 37° C. and 5% $CO_2$, and then a CPE was observed; and $TCID_{50}$ was calculated by the Reed-Muench method, and a viral titer was shown in Table 3.

TABLE 3

Summary of titers of replication-restricted influenza viruses

| Virus name | Viral titer ($TCID_{50}$/mL) |
|---|---|
| rPR8-M2-del14 | 7.75 |
| rPR8-M2-del20 | 7.75 |
| rPR8-M2-del22 | 6.75 |
| rPR8-M2-del38 | 7.5 |
| rPR8-M2-del65 | 6.75 |
| rPR8-M2-del103 | 6.75 |

Example 4

Determination of Growth Curves of Replication-Restricted Influenza Viruses

Figure 3:
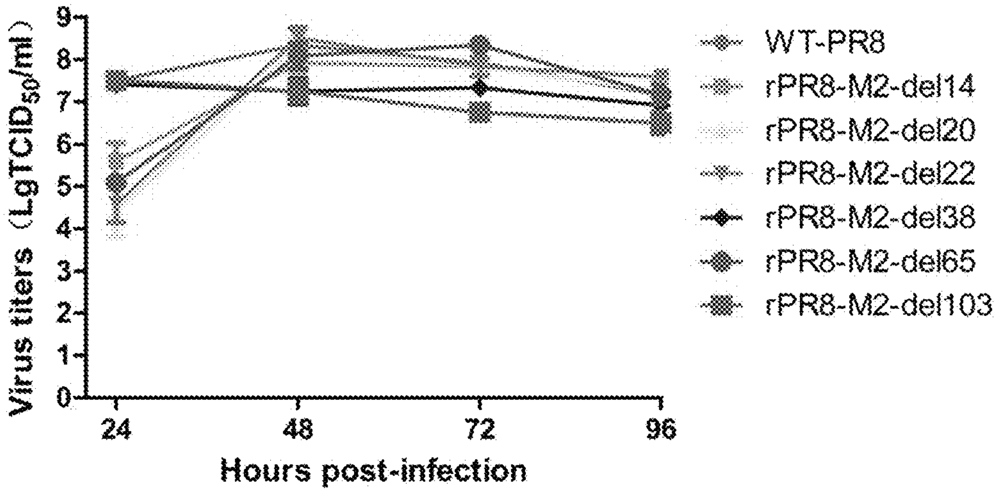
FIG. 3 shows growth curves of the replication-restricted viruses rPR8-M2-del14, rPR8-M2-del20, rPR8-M2-del22, rPR8-M2-del38, rPR8-M2-del65, and rPR8-M2-del103 and the parental virus IAV PR8 according to the present disclosure.

The M2 protein-expressing MDCK cell was inoculated into a 48-well plate; after the cell grew to form a monolayer, the replication-restricted influenza viruses rPR8-M2-del14, rPR8-M2-del20, rPR8-M2-del22, rPR8-M2-del38, rPR8-M2-del65, and rPR8-M2-del103 and the parental virus IAV PR8 were used to infect the cell at an MOI of 0.001, where 3 replicates were set for each group; the cell was cultivated in a 37° C. and 5% $CO_2$ incubator; a virus was collected at 24 h, 48 h, 72 h, and 96 h after the infection, virus solutions collected at different time points each were continuously diluted 10-fold, where 3 replicates were set for each dilution ratio, a resulting dilution was added to an M2 protein-expressing MDCK cell growing to form a monolayer in a 96-well plate, and the cell was cultivated in a cell culture incubator at 37° C. and 5% $CO_2$ for 72 h; a CPE was observed, and $TCID_{50}$ was calculated by the Reed-Muench method; and data analysis was conducted, and then a growth curve of a replication-restricted influenza virus was plotted (FIG. 3). It can be seen from FIG. 3 that rPR8-M2-del14, rPR8-M2-del20, rPR8-M2-del22, rPR8-M2-del65, and WT-PR8 have similar growth characteristics and can achieve similar viral titers after infection for 48 h, and rPR8-M2-del38 and rPR8-M2-del103 can also exhibit prominent growth characteristics on the M2 protein-expressing MDCK cell.

Example 5

Figure 4:
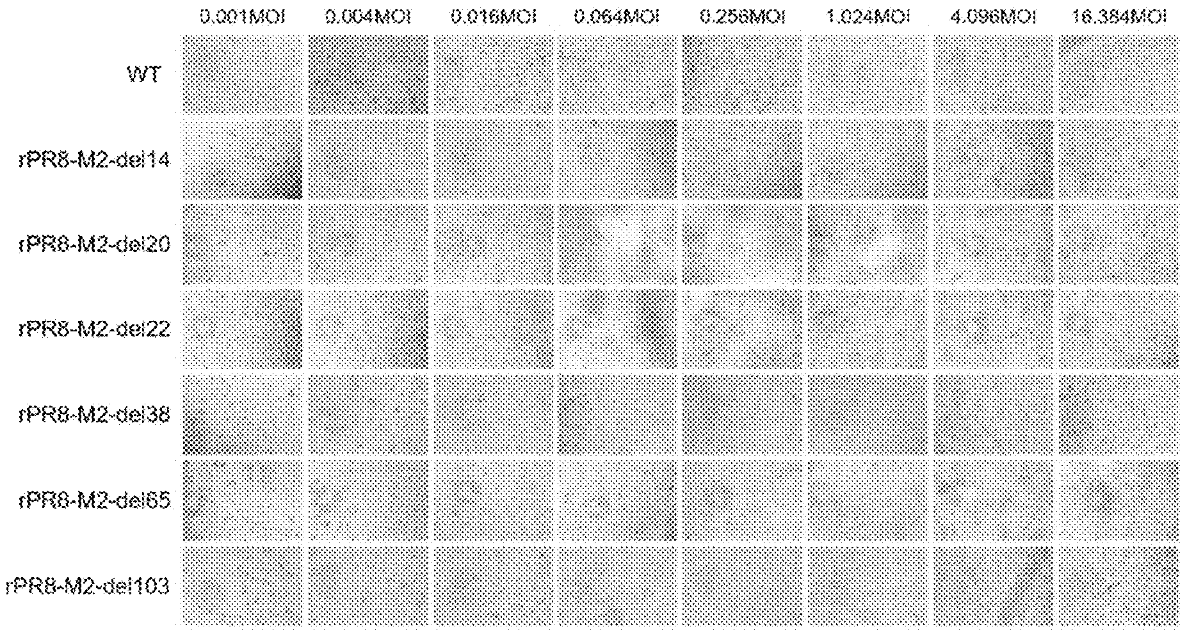
FIG. 4 shows cytopathic effects (CPEs) of MDCK cells infected with the replication-restricted viruses rPR8-M2-del14, rPR8-M2-del20, rPR8-M2-del22, rPR8-M2-del38, rPR8-M2-del65, and rPR8-M2-del103 and the parental virus IAV PR8 for 72 h at different multiplicities of infection (MOIs) according to the present disclosure.
Figure 5:
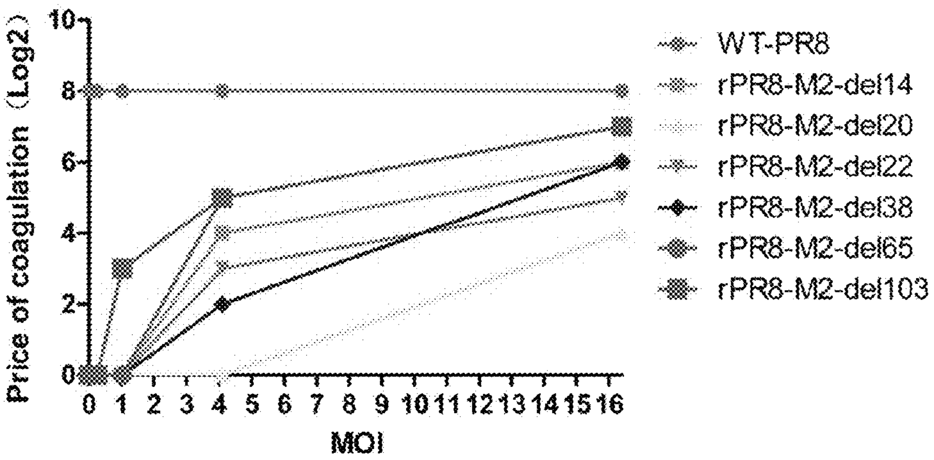
FIG. 5 shows CRBC agglutination titers of MDCK cells infected with the replication-restricted viruses rPR8-M2-del14, rPR8-M2-del20, rPR8-M2-del22, rPR8-M2-del38, rPR8-M2-del65, and rPR8-M2-del103 and the parental virus IAV PR8 for 72 h at different MOIs according to the present disclosure.

Determination of Growth of Replication-Restricted Influenza Viruses in an MDCK Cell An MDCK cell was inoculated into a 48-well plate; after the cell grew to form a monolayer, the replication-restricted influenza viruses rPR8-M2-del14, rPR8-M2-del20, rPR8-M2-del22, rPR8-M2-del38, rPR8-M2-del65, and rPR8-M2-del103 and the parental virus IAV PR8 each were used to infect the cell at MOIs of 0.001, 0.004, 0.016, 0.064, 0.256, 1.024, 4.096, and 16.384, and the cell was cultivated in a 37° C. and 5% $CO_2$ incubator for 72 h; a CPE was observed, and the cell was photographed (FIG. 4 shows CPEs of MDCK cells infected with the replication-restricted influenza viruses rPR8-M2-del14, rPR8-M2-del20, rPR8-M2-del22, rPR8-M2-del38, rPR8-M2-del65, and rPR8-M2-del103 and the parental virus IAV PR8 for 72 h at different MOIs); the cell was repeatedly frozen and thawed three times, then the plate was centrifuged, a resulting supernatant was collected and subjected to a chicken red blood cell (CRBC) agglutination test, and a CRBC agglutination titer was recorded (FIG. 5 shows CRBC agglutination titers of MDCK cells infected with the replication-restricted viruses rPR8-M2-del14, rPR8-M2-del20, rPR8-M2-del22, rPR8-M2-del38, rPR8-M2-del65, and rPR8-M2-del103 and the parental virus IAV PR8 for 72 h at different MOIs). Experimental results showed that the replication-restricted influenza viruses at high doses grew well on the MDCK cell. It can be seen from FIG. 5 that an attenuation effect of the rPR8-M2-del20 virus is obvious, indicating that the replication-restricted influenza virus obtained by the present disclosure is not absolutely dependent on the M2 protein-expressing MDCK cell line.

Stock solutions of the replication-restricted influenza viruses rPR8-M2-del14, rPR8-M2-del20, rPR8-M2-del22, rPR8-M2-del38, rPR8-M2-del65, and rPR8-M2-del103 each were inoculated into 4 chicken embryos; and 72 h later, an allantoic fluid of a chicken embryo was collected and subjected to a CRBC agglutination test, and a CRBC agglutination titer was recorded (Table 4). The rPR8-M2-del20 virus with the optimal attenuation effect can replicate in the chicken embryos and achieve a high CRBC agglutination titer, indicating that the replication-restricted influenza virus of the present disclosure can be produced in large quantities with a chicken embryo, which reduces the cost and increases the yield.

TABLE 4

CRBC agglutination titers of chicken embryos infected with the replication-restricted influenza viruses

| Virus name | Agglutination titer 1 ($2^n$) | Agglutination titer 2 ($2^n$) | Agglutination titer 3 ($2^n$) | Agglutination titer 4 ($2^n$) |
|---|---|---|---|---|
| rPR8-M2-del14 | 9 | 9 | 8 | 8 |
| rPR8-M2-del20 | 9 | 8.5 | 8 | 8 |
| rPR8-M2-del22 | 5.5 | 6 | 5 | 5 |
| rPR8-M2-del38 | 7 | 7 | 6 | 8.5 |
| rPR8-M2-del65 | 8 | 8.5 | 8 | 8 |
| rPR8-M2-del103 | 8 | 7 | 8 | 7.5 |

Example 6

Figure 6:
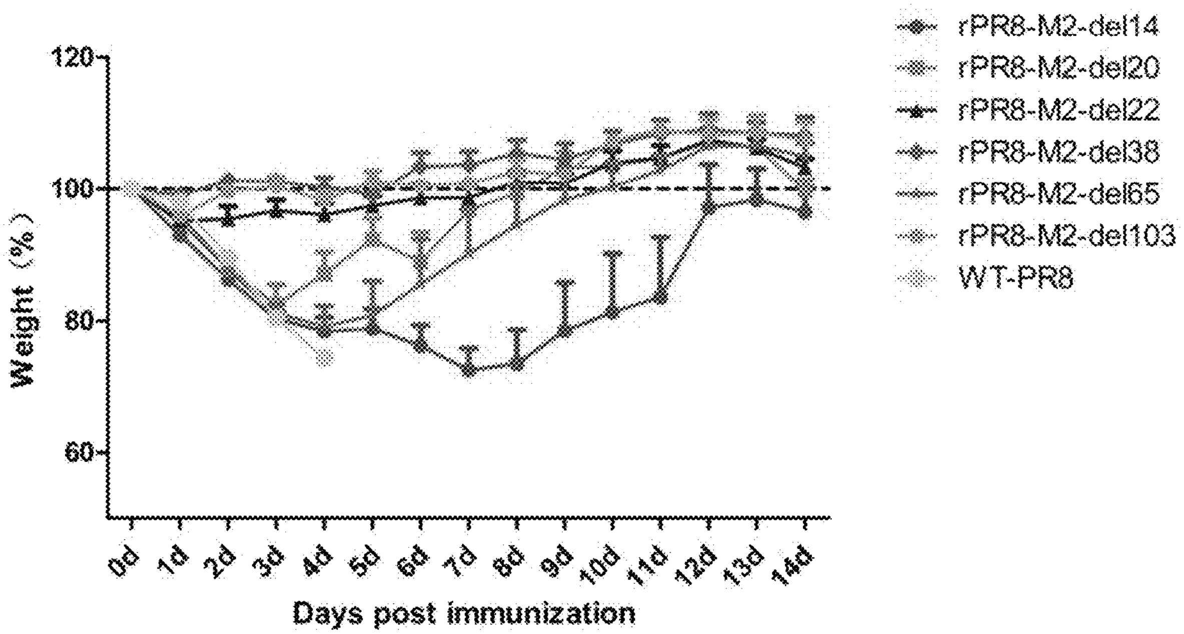
FIG. 6 shows body weight changes of mice within 14 d after immunization with the replication-restricted viruses rPR8-M2-del14, rPR8-M2-del20, rPR8-M2-del22, rPR8-M2-del38, rPR8-M2-del65, and rPR8-M2-del103 and the parental virus IAV PR8 according to the present disclosure.
Figure 7:
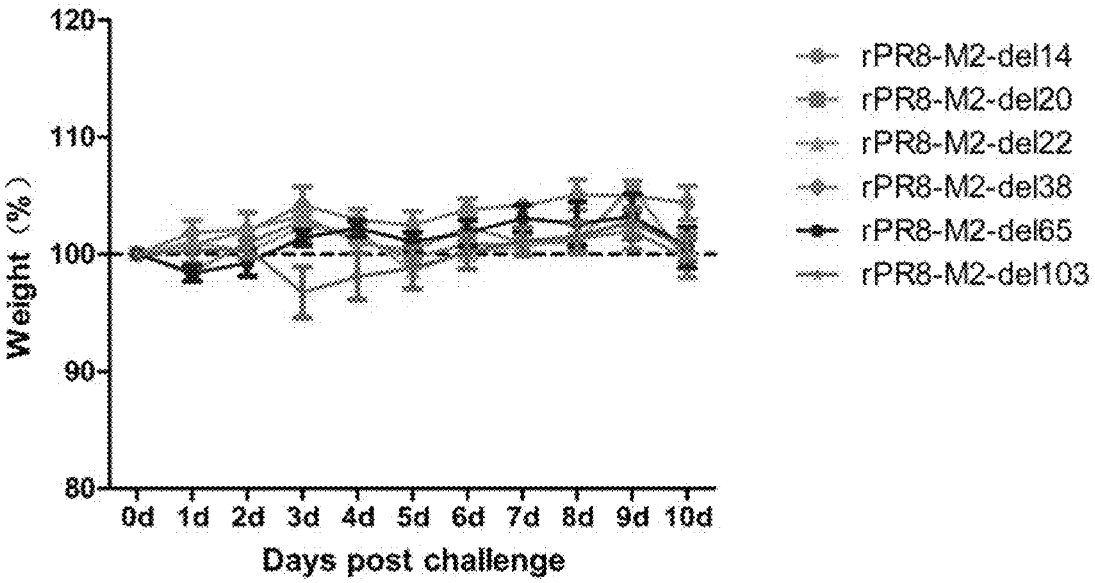
FIG. 7 shows body weight changes of mice within 10 d after the attack of the virus IAV PR8.

Immunization Experiment of Replication-Restricted Viruses 4-5 week-old Balb/C female mice were divided into 7 groups, with 8 mice in each group. The mice each were subjected to intranasal immunization with the replication-restricted viruses rPR8-M2-del14, rPR8-M2-del20, rPR8-M2-del22, rPR8-M2-del38, rPR8-M2-del65, and rPR8-M2-del103 and the parental virus IAV PR8 at $TCID_{50}$ of $10^6$, and 3 d after the immunization, 3 mice were selected from each group and sacrificed, and turbinates and lungs were collected and ground; and a ground tissue was taken and tested for a viral load by the same determination method as in Example 3, and $TCID_{50}$ was calculated by the Reed-Muench method. Viral titers were shown in Table 5. A body weight of each of the remaining 5 mice in each group was measured and recorded daily for 14 d, and a body weight change curve of mice was plotted (FIG. 6). It was found that, compared with the WT-PR8 virus, a body weight of the mice immunized with the viruses rPR8-M2-del14, rPR8-M2-del20, and rPR8-M2-del65 first decreased and then increased, a body weight of the mice immunized with the viruses rPR8-M2-del22, rPR8-M2-del38, and rPR8-M2-del103 fluctuated slightly, and the mice immunized with the virus WT-PR8 all died on day 5 after the immunization, indicating that the replication-restricted influenza virus of the present disclosure was non-pathogenic to mice; and a serum HI titer on day 14 after the immunization was 26.5 to 210 (Table 6), indicating that the attenuated influenza virus strain had a prominent immunization effect. Moreover, 21 d after the immunization, the WT-PR8 strain was used to infect the mice at $TCID_{50}$ of 106, then a body weight of each of the mice was measured and recorded daily for 10 d, and a body weight change curve of mice was plotted (FIG. 7). It can be seen from FIG. 7 that a body weight of the mice immunized with the viruses rPR8-M2-del14, rPR8-M2-del22, and rPR8-M2-del38 fluctuated slightly after the infection, indicating that these three attenuated influenza viruses have a prominent protective effect, which lays a foundation for the screening of safe and effective IAV live-attenuated vaccines.

TABLE 5

Replication of replication-restricted influenza viruses in mice

| Virus name | Immunization dose (TCID50) | Immunization time (d) | Viral titer (TCID50/mL) Turbinate | Viral titer (TCID50/mL) Lung |
|---|---|---|---|---|
| rPR8-M2-del14 | $10^6$ | 3 | 0; 0; 0 | 4.75; 4.5; 3.75 |
| rPR8-M2-del20 | $10^6$ | 3 | 0; 0; 0 | 0; 4.5; 0 |
| rPR8-M2-del22 | $10^6$ | 3 | 0; 0; 1.98 | 0; 1.98; 0 |
| rPR8-M2-del38 | $10^6$ | 3 | 3.25; 0; 0 | 0; 0; 0 |
| rPR8-M2-del65 | $10^6$ | 3 | 0; 0; 0 | 0; 0; 0 |
| rPR8-M2-del103 | $10^6$ | 3 | 0; 2.75; 0 | 0; 0; 0 |

TABLE 6

HI titers of mice immunized with the replication-restricted influenza viruses

| Virus name | Immunization dose (TCID50) | Immunization time (d) | HI titer Mouse 1 | HI titer Mouse 2 | HI titer Mouse 3 | HI titer Mouse 4 | HI titer Mouse |
|---|---|---|---|---|---|---|---|
| rPR8-M2-del14 | $10^6$ | 14 | $2^{10}$ | $2^9$ | $2^9$ | $2^8$ | $2^8$ |
| rPR8-M2-del20 | $10^6$ | 14 | $2^9$ | $2^8$ | $2^8$ | $2^8$ | $2^8$ |
| rPR8-M2-del22 | $10^6$ | 14 | $2^7$ | $2^7$ | $2^{6.5}$ | $2^7$ | $2^7$ |
| rPR8-M2-del38 | $10^6$ | 14 | $2^7$ | $2^{9.5}$ | $2^{8.5}$ | $2^8$ | $2^7$ |
| rPR8-M2-del65 | $10^6$ | 14 | $2^{9.5}$ | $2^{8.5}$ | $2^8$ | $2^9$ | $2^8$ |
| rPR8-M2-del103 | $10^6$ | 14 | $2^8$ | $2^7$ | $2^8$ | $2^8$ | $2^8$ |

The above are merely preferred implementations of the present disclosure. It should be noted that several improvements and modifications may further be made by a person of ordinary skill in the art without departing from the principle of the present disclosure, and such improvements and modifications should also be deemed as falling within the protection scope of the present disclosure.

What is claimed is:

1. An attenuation method of an influenza virus, consisting of the following step: deleting a number of bases within positions 73-189 of the coding region of an M2 protein in a conserved region of the influenza virus to obtain an attenuated influenza virus with a corresponding base deletion, wherein the coding region of the M2 protein is the nucleotide sequence of SEQ ID NO: 7, and the deletion is selected from the group consisting of:

(a) deletion of the 14 bases from position 73 to position 86 of SEQ ID NO: 7;

(b) deletion of the 20 bases from position 87 to position 106 of SEQ ID NO: 7;

(c) deletion of the 22 bases from position 130 to position 151 of SEQ ID NO: 7;

(d) deletion of the 38 bases from position 152 to position 189 of SEQ ID NO: 7;

(e) deletion of the 65 bases from position 87 to position 151 of SEQ ID NO: 7; and (f) deletion of the 103 bases from position 87 to position 189 of SEQ ID NO: 7.

2. The attenuation method according to claim 1, wherein the influenza virus is A/Puerto Rico/8/1934.

3. An attenuated influenza virus strain prepared by the attenuation method according to claim 1.

4. The attenuated influenza virus strain according to claim 3, wherein the influenza virus is A/Puerto Rico/8/1934.

* * * * *